United States Patent [19]
Bowers

[11] Patent Number: 5,682,879
[45] Date of Patent: Nov. 4, 1997

[54] FILTER MASK WITH EYE SHIELD

[75] Inventor: John Lawrence Bowers, Douglas, Isle of Man

[73] Assignee: Racal Health & Safety Limited, England

[21] Appl. No.: 684,273

[22] Filed: Jul. 17, 1996

[30] Foreign Application Priority Data

Aug. 4, 1995 [GB] United Kingdom ............. 9515987

[51] Int. Cl.⁶ ............................................ A62B 7/10
[52] U.S. Cl. ...................... 128/206.19; 128/206.21; 128/206.23; 128/201.12; 128/857
[58] Field of Search .............. 128/205.27, 205.29, 128/206.12, 206.13, 206.14, 206.19, 206.16, 206.17, 206.18, 206.21, 206.23, 206.27, 206.28, 206.24, 201.12, 201.15, 201.17; 2/206, 173

[56] References Cited

U.S. PATENT DOCUMENTS

| | | | |
|---|---|---|---|
| 2,056,753 | 10/1936 | Wagner | 128/206.19 |
| 4,944,294 | 7/1990 | Borek | 128/201.17 |
| 4,966,140 | 10/1990 | Herzberg | 2/206 |
| 5,383,450 | 1/1995 | Hubbard et al. | 128/206 |
| 5,406,943 | 4/1995 | Hubbard et al. | 128/201.17 |
| 5,406,944 | 4/1995 | Gazzara | 128/206 |
| 5,446,925 | 9/1995 | Baker et al. | 2/173 |
| 5,553,608 | 9/1996 | Reese et al. | 128/206.21 |
| 5,561,863 | 10/1996 | Carlson | 128/863 |
| 5,584,078 | 12/1996 | Saboory | 128/857 |

FOREIGN PATENT DOCUMENTS

| | | |
|---|---|---|
| 0650712A1 | 3/1995 | European Pat. Off. . |
| 2046102 | 12/1980 | United Kingdom . |
| 10106 | 2/1989 | WIPO ............. 128/206.19 |

Primary Examiner—Vincent Millin
Assistant Examiner—William J. Deane, Jr.
Attorney, Agent, or Firm—Pedro P. Hernandez

[57] ABSTRACT

A filter mask has an eye shield comprising a sheet of flexible transparent material sealed to the mask along its lower edge. That edge of the eye shield material has one or more widthwise folds so that, while the upper edge of the mask can follow the contours over the nose and along the cheeks of a user the eye shield can adopt a more gentle curvature by relative compression of the folds where they pass over the nose and relative opening of the folds to each side. A comfortable fit can thereby be achieved without creasing of the eye shield and without detriment to the sealing of the mask against the user's face and the sealing of the eye shield to the mask.

5 Claims, 3 Drawing Sheets

FILTER MASK WITH EYE SHIELD

BACKGROUND OF THE INVENTION

The present invention relates to personal protection devices and more particularly to filter masks, by which term we mean a device adapted to be worn over the nose and mouth of a user and made from or incorporating a filter material to remove one or more unwanted components from the inspired and/or expired air. Filter masks are used by personnel in various occupations where it is necessary to work for example in dusty or mist-laden environments, or where there is a risk of bacterial or other microbiological contamination e.g. in hospitals and prisons. In such cases the filtered-out components are of a particulate nature. However, masks incorporating suitable filter materials are also of course well known for use in protecting the wearer from unwanted gaseous or vapour components and the term "filter material" is to be construed herein, when the context so permits, as including any material which is adapted to remove an unwanted component of whatever phase from air flowing through it, whether physically, mechanically, electrostatically, chemically, by absorption, adsorption or by a combination of these or any other process.

The invention will be described particularly in the context of its application to the kind of low-cost, usually disposable (i.e. single-use) masks also referred to as "filtering facepieces". Known masks of this kind are typically in the form of semi-rigid cup-shaped elements, made by slip-moulding or by other forming techniques from suitable non-woven fibrous materials, or are formed by assembling or folding up flexible elements cut from woven or non-woven sheet materials having the desired filtering characteristics. A particularly preferred example of the latter is the mask shaped in accordance with the invention in GB-2046102 and marketed by the Assignees of the present Applicant under the trade mark DELTA.

While the principal purpose of any such mask is of course to prevent contaminants entering the wearer's respiratory system and/or to protect those around him from any contaminants in his exhalate, there is also in various circumstances a need to protect the wearer's eyes from contamination. In particular, during a surgical procedure there is the danger that disease can be passed if contaminated body fluids should accidentally become splashed or sprayed into the surgeon's or other attendants' eyes; similar dangers may also arise e.g. in laboratories where such fluids may be handled. To counter this threat it is accordingly known to equip a filter mask of the kind worn by such personnel with a transparent eye shield.

The simplest way to modify a mask of this kind to provide protection also for the eyes is to attach a sheet of flexible transparent plastics material adjacent to the upper edge of the filter material forming the conventional mask, but unless appropriate attention is paid to the interface between the two parts of the combined device this will not achieve a satisfactory result. In particular, when in use it is important that the upper edge of the mask follows the contours of the wearer's face over his nose and along his cheeks to either side, to form a proper seal. If an attempt is made to make the overlapping lower edge of a simply-attached plastics sheet follow these same contours, however, certain problems will be encountered. Firstly, the plastics material will tend to crease around the nose region, with an obviously deleterious effect on its optical qualities. Secondly, the upper part of the plastics sheet will tend to press against or dig into the wearer's forehead, causing discomfort. In addition, the lower edge of the plastics sheet will tend to pull away from the wearer's cheeks, applying tension to the filter material which will likewise pull away if it can, thereby providing an air leakage path into and out of the mask.

In recognition of these problems a filter mask equipped with an eye shield is proposed in U.S. Pat. No. 5,383,450 where the eye shield is formed with a "keyhole" notch in its lower edge to facilitate bending, and it is bonded to the filter material only at two lateral positions, not along their entire overlapping edges. A certain amount of relative movement is therefore possible between the filter material and the eye shield, which are free to follow different contours where they overlap. A disadvantageous consequence, however, is that gaps can form between their overlapping edges, which provide a possible route through which splashed body fluids can reach the wearer's eyes. Another approach is shown in EP-0650712. This again has a contoured eye shield bonded only at two lateral positions to the filter material. In addition, tie tapes or an elastic band are attached to the sides of the eye shield and by adjusting the angle at which the tapes or band pass over the wearer's head the angular position of the upper portion of the eye shield can be adjusted. In U.S. Pat. No. 5,406,944 an eye shield is attached to a filter mask by a pair of malleable strips so that the whole of the eye shield can be moved to a selected distance away from the wearer's face. This will, however, leave a wide gap between the overlapping edges of the mask and eye shield through which contaminants might pass.

SUMMARY OF THE INVENTION

The present invention adopts a different approach to the task of attaching an eye shield to a filter mask in such a way as to overcome the aforesaid problems. In accordance with the invention there is provided a mask made from or incorporating a filter material and adapted to be worn over the nose and mouth of a user; the mask having an upper edge which in use can follow the contours of a human face over the nose and along the cheeks to either side; and an eye shield comprising a sheet of flexible plastics material at least an upper portion of which is transparent; said sheet overlapping said upper edge of the mask and the lower edge of said sheet being sealed to the mask; and said lower edge having one or more widthwise folds whereby, in use, said fold(s) are relatively closed where they pass over the user's nose but relatively open to each side of the user's nose to space the corresponding portions of the eye shield forwardly of the contour of the upper edge of the mask.

By virtue of the aforesaid folded construction of the eye shield, problems of creasing, interference with the user's forehead and tension of the filter material can be overcome in use of a mask in accordance with the invention. At the same time the lower edge of the plastics sheet can be sealed to the mask across substantially its entire width of overlap, thereby eliminating the risk of splashes reaching the user's eyes through the gaps inherent in the prior art constructions. Neither is it necessary to attach any tie tapes or the like to the eye shield itself and to rely on the user adjusting the angle of the eye shield when it is donned.

BRIEF DESCRIPTION OF THE DRAWINGS

The invention will now be more particularly described, by way of example, with reference to the accompanying drawings, in which.

DETAILED DESCRIPTION OF THE PREFERRED EMBODIMENT

Figure 1:
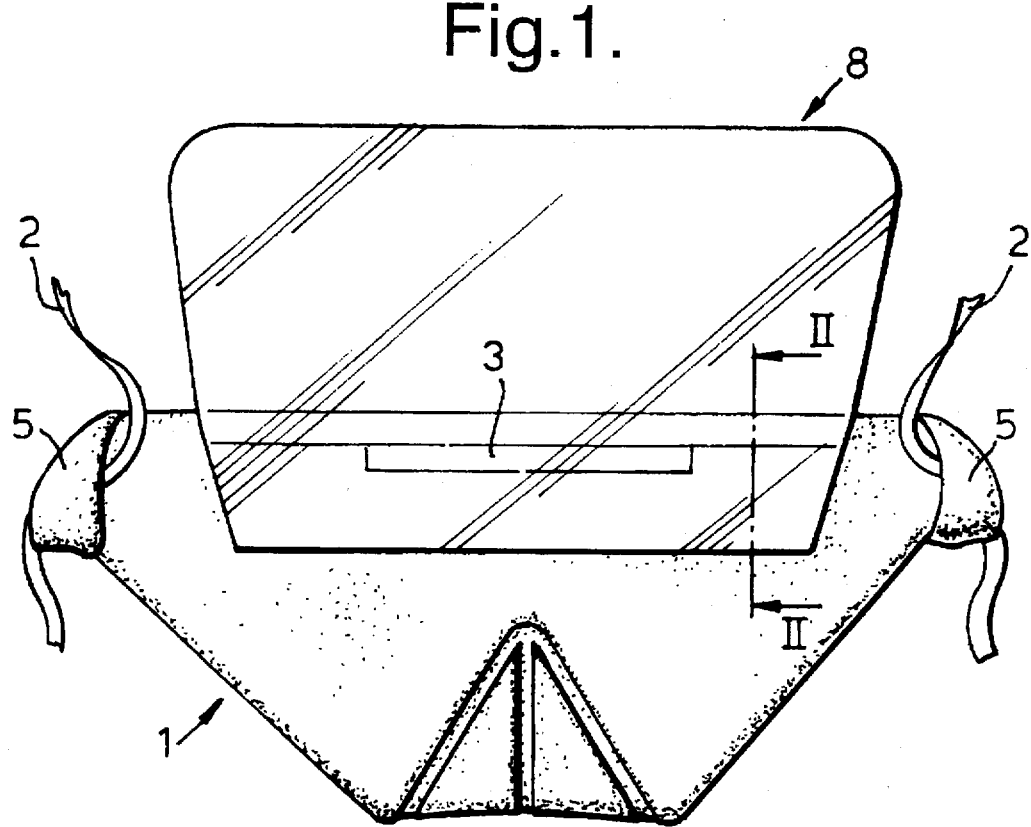
FIG. 1 is a plan view of a preferred embodiment of an eye shield-equipped filter mask according to the invention, in an inoperative condition.
Figure 3:
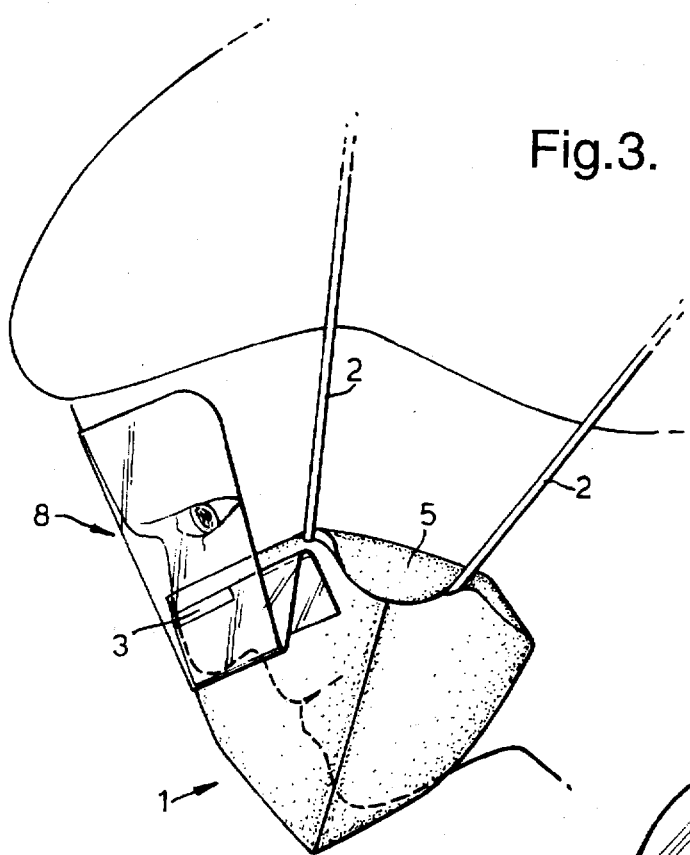
FIG. 3 is a side view of the mask in use.
Figure 4:
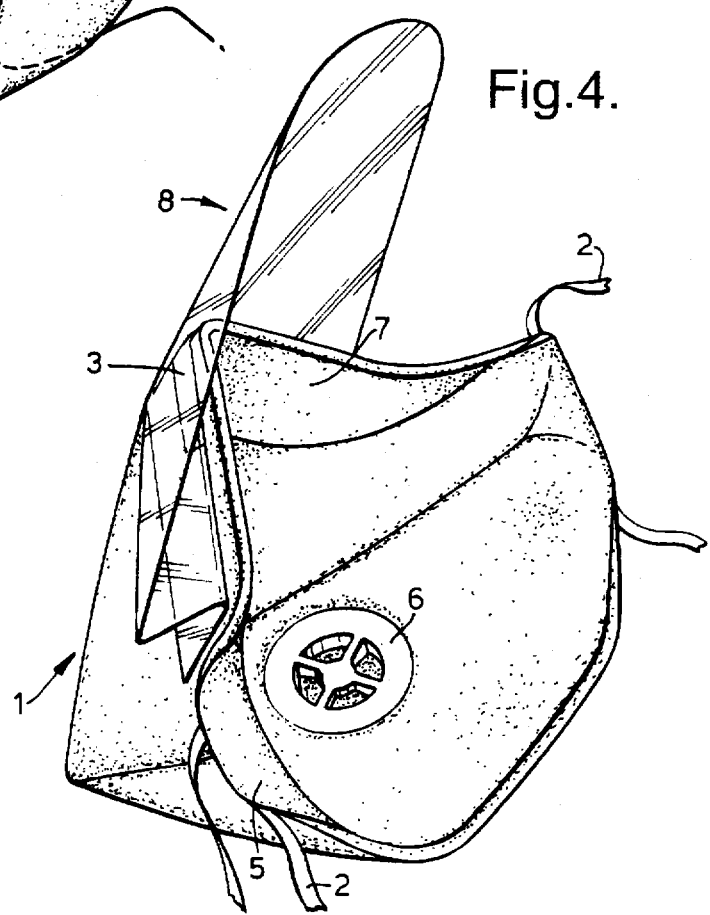
FIG. 4 is a perspective view of the mask from a position above and to the rear of one side, in its operative configuration.

The mask 1 shown in the drawings is made from one or more layers of flexible sheet filter material cut from a blank, folded and welded to form in its operative configuration a cup shape adapted to be worn over the nose and mouth of the user. In the preferred embodiment it is in particular shaped in accordance with the invention in GB-2046102, to which reference is directed for a fuller description of the method of forming the mask from a flat blank. Briefly, however, it can be folded flat to a trapezial platform as illustrated in FIG. 1 for packing, transportation and storage prior to use, and then opened out into a cup shape as illustrated in FIGS. 3 and 4 when required for use. In use the peripheral edge of the mask forms a seal against the wearer's face and it is held in place by elastic headbands 2 and a deformable wire nose clip 3 as well known in the art. In the illustrated embodiment there is a continuous elastic band 2 passing through loops 5 formed at each side of the mask by folding forwardly the outermost portion of material and welding it to the facing portion. An exhalation valve 6 is also seen in FIG. 4, and a foam pad 7 is attached inside the mask along its upper edge to improve the comfort and sealing in the region of the user's nose. FIG. 4 illustrates the configuration of the mask as it would be fitted to the user's face, from which it is seen that the upper edge of the mask material is formed into a sharp convex curve where it passes over the bridge of the nose, with a more gentle concave curvature to each side where it passes over the user's cheeks.

The material from which the mask 1 is made may in principle be any known flexible sheet filter material selected for the required removal of airborne contaminants. In this embodiment it also includes a layer of known material which is pervious to air but impervious to the passage of liquids in the direction from the exterior to the interior of the mask, to protect the wearer in the case of e.g. contaminated body fluids coming into contact with the mask. To protect his eyes from contact with such fluids which might be splashed or sprayed towards his face e.g. during a surgical procedure, the mask is also equipped with an eye shield 8.

Figure 2:
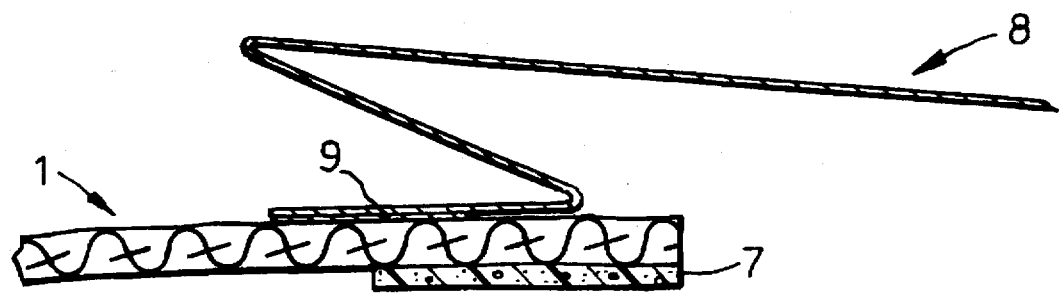
FIG. 2 is a fragmentary sectional view, on the line II—II in FIG. 1, through the attachment of the eye shield to the mask.

The eye shield 8 is in the form of a thin sheet of flexible transparent plastics, such as acetate with a thickness in the range of 25μ–0.5 mm, preferably around 0.1 mm. Its lower edge is formed with two overlapping widthwise folds and is attached to the mask 1, in overlapping relation with the upper edge of the latter, across the full width of that edge of the eye shield. Double-sided adhesive tape 9 may serve for this attachment. The folds in the eye shield material serve to stiffen somewhat its lower edge against lateral bending. In the relaxed state of the folded edge, that is to say while the upper edge of the mask 1 remains flat as indicated in FIG. 1, and the eye shield 8 is otherwise unconstrained, these folds also cause the eye shield as a whole to float forwardly of the mask somewhat, as indicated in FIG. 2. When the mask is opened out and its upper edge is configured to fit the user's face, however, the lower edge of the eye shield material will be placed in tension.

Figure 5:
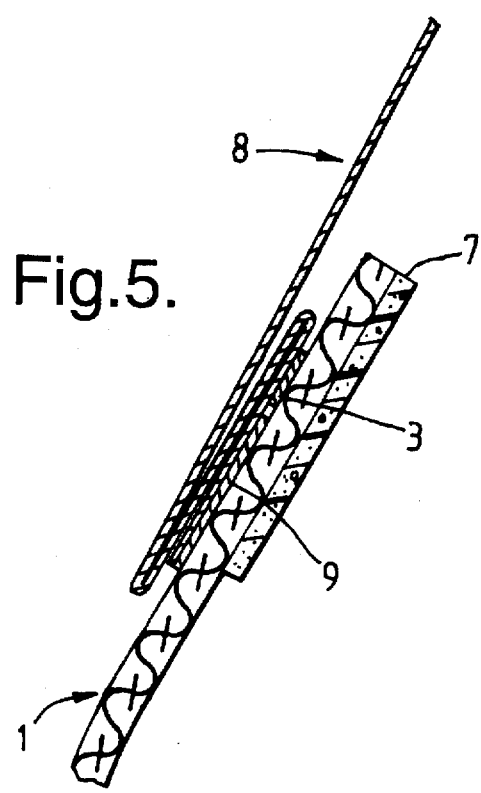
FIGS. 5 and 6 are fragmentary sectional views through the attachment of the eye shield to the mask at two different positions, in its operative configuration.
Figure 6:
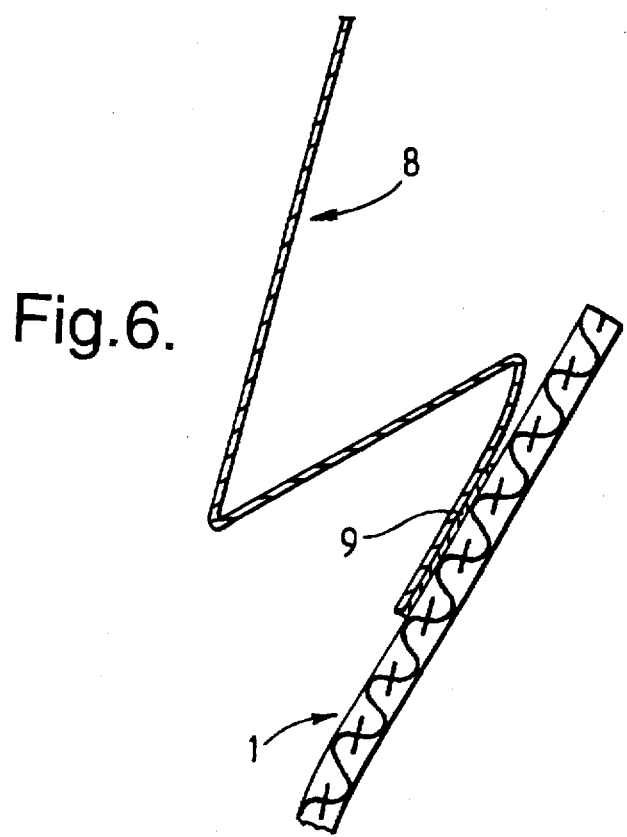

The effect of this when the mask is donned is indicated in FIGS. 3 and 4. That is to say, the presence of the folds in the eye shield material means that the shield bends around the user's face in a more gentle convex curvature than the curvature of the upper edge of the mask around his nose, the folds becoming compressed together at the bridge of the nose but remaining open—or even opening up to a greater extent than in the relaxed state—to each side. This is also illustrated in the sectional views of FIGS. 5 and 6 where FIG. 5 shows the folds compressed at the central region of the eye shield and FIG. 6 shows the folds open at its side edge. The shield 8 where it passes in front of the user's eyes is therefore spaced forwardly of the overlapping parts of the mask material. The result is a more favourable anatomical fit, with the upper portion of the eye shield just brushing the user's forehead without digging into or pressing hard against the same. The gentle bending of the eye shield also means that there is no tendency to crease around the user's nose, so its optical properties are unimpaired. This is all achieved, however, with a structure in which the lower edge of the eye shield remains sealed to the mask across its whole width and therefore involves no risk of splashed contaminants reaching the user's eyes from beneath that edge of the shield.

The material from which the eyeshield 8 is formed may be tinted or otherwise treated to reduce glare/reflections and/or to reduce misting. The material from which the mask 1 is made may also be of a dark colour to reduce glare.

I claim:

1. A mask made from or incorporating a filter material and adapted to be worn over the nose and mouth of a user; the mask having an upper edge which in use can follow the contours of a human face over the nose and along the cheeks to either side; and an eye shield comprising a sheet of flexible plastics material at least an upper portion of which is transparent; said sheet overlapping said upper edge of the mask and the lower edge of said sheet being sealed to the mask; and said lower edge having one or more widthwise folds whereby, in use, said fold(s) are relatively closed where they pass over the user's nose but relatively open to each side of the user's nose to space the corresponding portions of the eye shield forwardly of the contour of the upper edge of the mask.

2. A mask according to claim 1 wherein the lower edge of said sheet has two overlapping folds.

3. A mask according to claim 1 wherein the lower edge of said sheet is sealed to the mask across substantially its entire width of overlap.

4. A mask according to claim 1 made from flexible sheet filter material which in an inoperable condition can be folded flat and when required for use is adapted to be opened out into a cup shape with said upper edge following the contours of a human face as aforesaid, and wherein the action of said opening out causes said folds to be relatively closed and open as aforesaid.

5. An eye shield for a filter mask, comprising a sheet of flexible plastics material at least an upper portion of which is transparent and the lower edge of which has one or more widthwise folds, whereby when said eye shield is sealed to a filter mask in overlapping relationship with an upper edge thereof which follows the contours of a human face over the nose and along the cheeks to either side said fold(s) can be relatively closed where they pass over the nose but relatively open to each side thereof.

* * * * *